US012544248B1

(12) United States Patent
Beversluis

(10) Patent No.: US 12,544,248 B1
(45) Date of Patent: Feb. 10, 2026

(54) ANKLE FOOT ORTHOSIS

(71) Applicant: B6 Products, LLC, Grand Rapids, MI (US)

(72) Inventor: Gabriel D. Beversluis, Grand Rapids, MI (US)

(73) Assignee: B6 Products, LLC, Grand Rapids, MI (US)

( * ) Notice: Subject to any disclaimer, the term of this patent is extended or adjusted under 35 U.S.C. 154(b) by 55 days.

(21) Appl. No.: 18/522,395

(22) Filed: Nov. 29, 2023

Related U.S. Application Data

(60) Provisional application No. 63/430,024, filed on Dec. 4, 2022.

(51) Int. Cl.
*A61F 5/01* (2006.01)

(52) U.S. Cl.
CPC .... *A61F 5/0127* (2013.01); *A61F 2005/0155* (2013.01); *A61F 2005/0165* (2013.01)

(58) Field of Classification Search
CPC .... A61F 5/0127; A61F 5/0113; A61F 5/0193; A61F 5/0111; A61F 5/05; A61F 2005/0158; A61F 13/066; A61F 5/0102; A61F 5/0585; A61F 5/0106; A61F 5/0116; A61F 2/6607; A43B 7/20; A43B 7/22; A43B 5/1691; A43B 5/1683; A43B 5/1666; A43B 5/16
See application file for complete search history.

(56) References Cited

U.S. PATENT DOCUMENTS 4,669,142 A 6/1987 Meyer
4,756,096 A 7/1988 Meyer
6,860,864 B2 3/2005 Meyer
8,808,598 B1 8/2014 Meyer
9,398,970 B1 7/2016 Meyer
9,707,118 B1 * 7/2017 Meyer .................. A61F 5/0127
2003/0125653 A1 7/2003 Meyer
2004/0002672 A1 1/2004 Carlson
2015/0126911 A1 5/2015 Abramowicz et al.
2018/0055713 A1 3/2018 Cromie et al.
2020/0383815 A1 12/2020 Hinshon

FOREIGN PATENT DOCUMENTS

CN 108542566 A 9/2018
WO WO-2022032149 A1 * 2/2022 ............... A61F 2/66

* cited by examiner

*Primary Examiner* — Ophelia A Hawthorne
(74) *Attorney, Agent, or Firm* — Corner Counsel, LLC

(57) ABSTRACT

An ankle foot orthosis comprises an upper portion configured for placement on a lower leg and a lower portion configured for placement on a foot, connected to one another at at least one joint. A strap attached to the upper portion and the lower portion includes at least a portion that is elastic, and a ratchet mechanism allows an incremental increase in stretching the elastic and being releasable to release all tension.

19 Claims, 12 Drawing Sheets

ANKLE FOOT ORTHOSIS

CROSS-REFERENCE TO RELATED APPLICATIONS

The present application claims the benefit of U.S. Provisional Application No. 63/430,024, filed Dec. 4, 2022.

TECHNICAL FIELD

The invention generally relates to an ankle foot orthosis and therapeutic procedures using the ankle foot orthosis. Additionally, the invention relates to improved components for use with an ankle foot orthosis.

BACKGROUND

An ankle foot orthosis ("AFO") is designed for increasing the range of motion and correcting the alignment of a patient's foot and ankle. A patient's foot and ankle alignment may have lost range of motion at the ankle and become misaligned due to conditions such as cerebral palsy, injury, or other similar types of medical disorders.

With particular regard to children, if the misalignment between the foot and ankle is not corrected, this condition will likely lead to a permanent condition or deformity as the child ages.

Current ankle foot orthoses used to improve range of motion and correct such misalignment are expensive to purchase, heavy, bulky, and lack durability. They require tools to operate and are prone to breakage. Therefore, it is desirable to provide an improved ankle foot orthosis.

In particular, currently available orthosis components used for bracing, including the Stretching AFO from Ultraflex Systems and Multimotion from Allard USA, Inc., are: 1) expensive to purchase and may not be covered by insurance because of cost; 2) heavy and bulky and not ideal for pediatric applications; 3) lacking in durability and prone to breakage; and 4) requiring tools to adjust. Therefore, it is desirable to provide for lower cost orthosis components and, ultimately, a lower cost ankle foot orthosis. Additionally, it is desirable to provide an ankle foot orthosis that is light in weight and may be used for pediatric patients. Finally, it is desirable to have an ankle foot orthosis with improved durability.

Other current common stretching ankle foot orthosis use "stretching straps" which extend from the calf to the forefoot to create a stretch. For example, a product manufactured by Cascade Dafo Inc. is the Cascade #9 Stretching AFO; however, this product does not allow plantar flexion while pushing against the resilience of the strap. This can lead to poor compliance and lack of improvement in range of motion. Additionally, such stretching straps do not provide the progression into the improved joint position while in use. Additionally, stretching strap AFOs do not provide a numerical indicator to track progress and limb position. Therefore, providing for an ankle foot orthosis that permits dynamic stretching, is adjustable, and provides a numerical indicator for the patient.

Other AFOs such as "Rooster Boot" are known to require tools to adjust and release tension. Such additional tools complicate usage and adoption by a patient. The disclosure of U.S. Pat. No. 9,398,970 is hereby incorporated by reference herein. Moreover, such AFOs may require two separate components, a first component anterior to the ankle to provide stretch, and a second component behind the ankle to "lock" the tension at a fixed position. Therefore, it is desirable to provide for a simplified ankle foot orthosis having a straightforward operation.

SUMMARY

In an aspect, an ankle foot orthosis ("AFO") comprises an upper portion configured for placement on a lower leg. The AFO has a lower portion configured for placement on a foot, the upper portion and lower portion are attached to one another by a lateral joint and a medial joint. The lateral joint and medial joint allow rotation of the upper portion with respect to the lower portion. The AFO has a strap, at least a portion of the strap is an elastic portion. The strap has a ratchet mechanism allowing an incremental increase in stretching the elastic portion of the strap. The ratchet mechanism is releasable to release all tension. A first end of the strap is connected to the upper portion offset from and anterior to the lateral joint and the medial joint, and a second end of the strap is connected to the lower portion offset from and anterior to the lateral joint and the medial joint.

In certain embodiments, the strap has a first strap that is inelastic and a second strap that is elastic. The upper portion can have a shell and an inner support structure. The upper portion can have a proximal flare.

In certain embodiments, the upper portion has a strap extending from a first side of the upper portion to a second side of the upper portion. The upper portion, in embodiments, has a support structure having a vertical portion. The vertical portion can comprise a metal bar. The support structure has, in embodiments, a horizontal portion extending proximally.

In embodiments, the support structure has a lower end attached to the lower portion. The lower end of the support structure can have a first bar and a second bar, the first bar may be disposed at an angle with respect to the second bar. For example, the lower end of the support structure can be generally Y-shaped.

The upper portion has an anterior projection that is, in embodiments, offset from a longitudinal axis aligned with the lateral joint and the medial joint. In embodiments, the lateral joint can limit rotation of the upper portion with respect to the lower portion to twenty degrees in a forward direction and twenty degrees in a rearward direction. In embodiments, the limit on rotation in one or both directions is adjustable.

In embodiments, the ratchet mechanism is a ratchet buckle having a button for releasing all tension when the button is pushed. The ratchet buckle can have a rotatable handle. The handle can be a rotatable knob. The upper portion, in embodiments, has an anterior projection, the first end of the strap being connected to the anterior projection.

In embodiments, the AFO has an inner boot. In embodiments, at least one of the lateral joint and the medial joint has a goniometer.

In a further aspect, the ankle foot orthosis comprises an upper portion configured for placement on a lower leg, the upper portion having an anterior projection. The orthosis can have a lower portion configured for placement on a foot. The upper portion can have a support structure with a lower end connected to the lower portion with a first bar and a second bar; the first bar being disposed at an angle with respect to the second bar. The upper portion and lower portion can be attached to one another by a lateral joint and a medial joint, the lateral joint and medial joint allowing rotation of the upper portion with respect to the lower portion. The orthosis has a strap offset from the lateral joint and medial joint. The strap includes a first strap, a second strap, at least a portion of at least one of the first strap and second strap being elastic, and a ratchet mechanism connecting the first strap to the second strap. The ratchet mechanism permits an incremental increase in stretching the elastic of the at least a portion of at least one of the first strap and second strap through movement of a handle. The ratchet mechanism is releasable to release all tension. A first end of the first strap is connected to the anterior projection of the upper portion, a second end of the first strap extends through the ratchet mechanism, a first end of the second strap extends through the ratchet mechanism, and a second end of the second strap is connected to the lower portion.

In embodiments, the first strap is inelastic and the second strap is elastic. In embodiments, the upper portion has a shell and an inner support structure. The upper portion may have a proximal flare. In embodiments, the upper portion has a strap extending from a first side of the upper portion to a second side of the upper portion.

The support structure can have a vertical portion. The vertical portion, for example, comprises a metal bar. The support structure can have a horizontal portion extending proximally. In embodiments, the lower end of the support structure is generally Y-shaped.

The anterior projection, in embodiments, is offset from a longitudinal axis aligned with the lateral joint and the medial joint.

In certain embodiments, the lateral joint limits rotation of the upper portion with respect to the lower portion to twenty degrees in a forward direction and twenty degrees in a rearward direction.

The orthosis can further comprise an inner boot. In embodiments, at least one of the lateral joint and the medial joint has a goniometer.

In a further aspect, a stretching strap for an orthosis is disclosed. The stretching strap includes a first strap, and a second strap; at least a portion of at least one of the first strap and second strap is elastic. The strap has a ratchet mechanism connecting the first strap to the second strap. The ratchet mechanism permits an incremental increase in stretching the elastic of the at least a portion of at least one of the first strap and second strap. The ratchet mechanism is releasable to release all tension. A first end of the first strap is arranged for connection to a portion of an orthosis, a second end of the first strap extends through the ratchet mechanism, a first end of the second strap extends through the ratchet mechanism, and a second end of the second strap is arranged for connection to another portion of the orthosis. In certain embodiments, the ratchet mechanism is a buckle having a button for releasing all tension when the button is pushed. In certain embodiments, the first strap is inelastic and the second strap is elastic. In certain embodiments, the ratchet mechanism has a rotatable handle. In embodiments, the handle is a rotatable knob.

In an aspect, a stretching strap for an orthosis has a first strap, a second strap, at least a portion of at least one of the first strap and second strap being elastic, and a ratchet mechanism connecting the first strap to the second strap. The ratchet mechanism permits an incremental increase in stretching the elastic of the at least a portion of at least one of the first strap and second strap. The ratchet mechanism is releasable to release all tension. A first end of the first strap is arranged for connection to a portion of an orthosis, a second end of the first strap extends through the ratchet mechanism, a first end of the second strap extends through the ratchet mechanism, and a second end of the second strap is arranged for connection to another portion of the orthosis. In certain embodiments, the ratchet mechanism is a buckle having a button for releasing all tension when the button is pushed in certain embodiments, or pulled out in other embodiments. In certain embodiments, the first strap is inelastic and the second strap is elastic. In certain embodiments, the ratchet mechanism has a handle. The handle may be a rotatable handle. In embodiments, the handle is a rotatable knob. In embodiments, the rotatable knob is pushed to release all tension.

An ankle foot orthosis and/or the stretching strap disclosed herein have many advantages. An ankle foot orthosis that provides for parents and juvenile patients to adjust as needed to either 1) increase the tension for greater stretching; or 2) to decrease the tension such as, for example, where musculature is contracted and there is a desire to improve patient comfort.

An ankle foot orthosis can be provided with a numeric scale to monitor the current stretching tension setting and to serve as a reference point for changes in tension and/or position.

An ankle foot orthosis can be provided with an easy method to "unlock" the tension strap in order to remove all tension from the patient's affected limb. With the strap unlocked, the orthosis can be properly applied to the patient. A patient's contracted limb is more easily placed into the orthosis with the strap unlocked.

The ankle foot orthosis, in embodiments, has a dynamic function which allows the patient to move against the resilience of the strap and actively extend their limb when they feel the need to stretch. The dynamic function also provides progressive movement to continually improve the position of the limb during use, without requiring adjustment.

The ankle foot orthosis has an adjustable function to allow for a slight incremental movement of the patient's limb. The patient's limb moves into improved angles for range of motion, improving during each session of use. Over time, as the patient's range of motion improves, the strap will continue to push the patient into an improved position. The combination of dynamic and adjustable tension allows for the orthosis to be used on patients with even more severe limitations on joint movement. The orthosis provides continual stretching therapy across at least 40 degrees of angular movement, from the position of 20 degrees in plantar flexion to 20 degrees in dorsiflexion.

A stretching strap is disclosed herein, which may be used with an ankle foot orthosis. The stretching strap may also be retrofitted into existing AFO's, knee braces, elbow braces, hip braces, et cetera. The stretching strap may include an elastomeric band, in embodiments. In embodiments, the stretching strap includes an elastomeric band connected to a rigid band, and having a ratcheting buckle.

Regardless of the application on an AFO or other device, the stretching strap provides: 1) a low cost option to achieve dynamic and adjustable stretching; 2) adjustability without requiring tools; 3) the ability to be retrofitted into multiple types of custom or prefabricated orthoses; 4) a ratcheting feature that allows for increasing tension until an effective stretch is obtained without complicated instructions; 5) a simple push button tension release to remove the tension (once tension is released the ratcheting feature can then be used to apply tension again); 6) a numeric scale for tension adjustment which allows for targeting appropriate stretching and goal setting; 7) a dynamic stretching strap which creates greater improvement in range of motion by gently pushing against the patients movement; 8) a stretching band that allows patients to move and extend their joints actively against tension, helping with specificity, patient discomfort, and the sensation of feeling trapped; 9) a lighter, less bulky device which is less likely to get tangled in sheets at night, less likely to bang on doors, furniture, or walls, and less likely to cause damage or breakage; 10) a device with easily replaceable parts; and 11) a goniometer for measuring the range of motion.

This summary is neither intended nor should be construed as being representative of the full extent and scope of the present disclosure. The present disclosure is set forth in various levels of detail in the summary as well as in the attached drawings and detailed description, and no limitation as to the scope of the present disclosure is intended by the inclusion of elements, or the exclusion of elements. Additional aspects of the present disclosure will become more readily apparent from the detailed description, particularly when taken together with the drawings.

The above-described benefits, embodiments, and or characterizations are not necessarily complete or exhaustive. Other benefits, embodiments, and or characterizations of the present disclosure are possible.

BRIEF DESCRIPTION OF THE DRAWINGS

The accompanying drawings, which are incorporated in and constitute a part of the present disclosure, illustrate preferred embodiments of the invention and, together with the description, serve to explain the present disclosure. Embodiments of the invention are in no way limited by the following figures.

DETAILED DESCRIPTION

Figure 1:
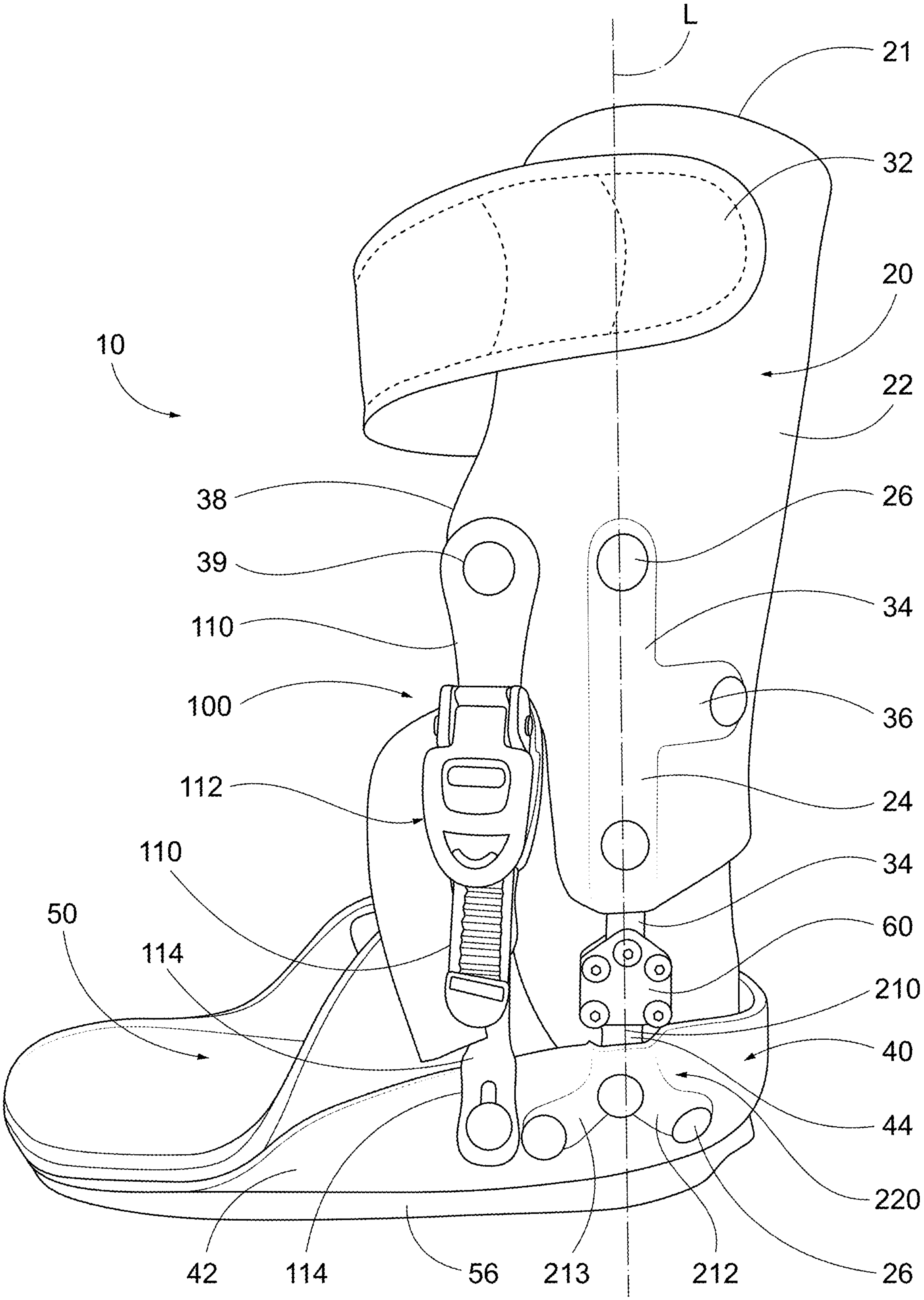
FIG. 1 is a lateral side elevation view of an ankle foot orthosis according to an embodiment, shown in a 90 degree or right angle orientation.
Figure 2:
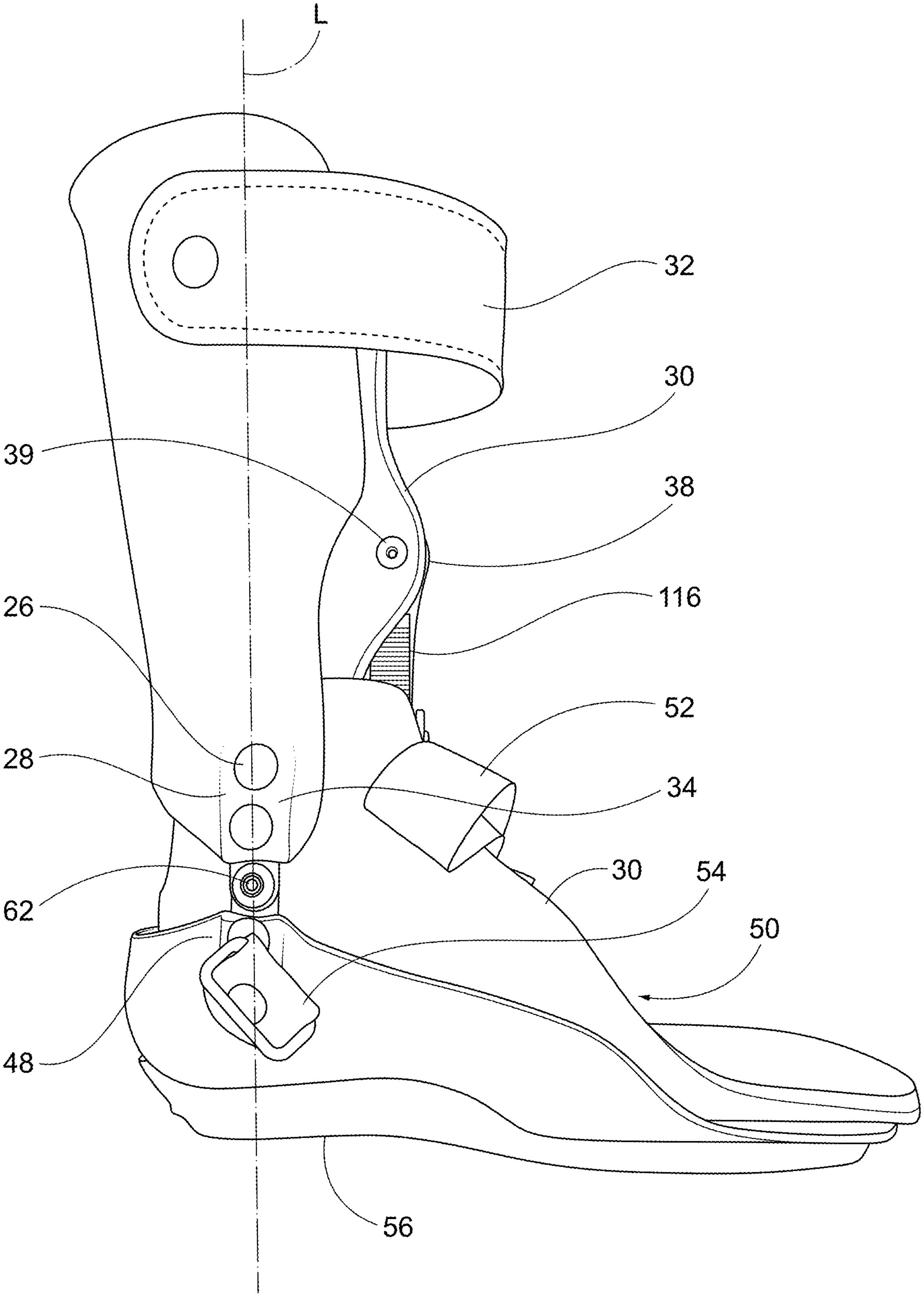
FIG. 2 is a medial side elevation view of the ankle foot orthosis of FIG. 1.

An ankle foot orthosis, for allowing a patient to engage in therapeutic stretching, is disclosed herein. Additionally, improved components are disclosed for use with an ankle foot orthosis.

Reference is made to FIGS. 1 through 5 which illustrate an ankle foot orthosis 10 including a stretching strap 100. In certain embodiments, the stretching strap 100 provides resistance against movement of the foot. In certain embodiments, the stretching strap is adjustable to provide different range of motion and/or different tension. In certain embodiments, the stretching strap 100 has a portion or portions that are elastic and which may provide greater tension as the strap 100 is stretched.

The ankle foot orthosis 10 has an upper or calf portion 20 and a lower or foot portion 40. Both portions include a shell 22, 42, respectively, which can be formed of rigid plastic or molded plastic.

The upper portion 20 has an outer support structure 24 and an inner support structure 28 attached to the shell 22 by connectors 26. A proximally extending flare 21 is provided on the upper portion 20, in embodiments. The orthosis 10, in certain embodiments, has an inner liner 30 made of flexible material such as a pliable foam to comfortably extend around the patient's calf. Extending from one side of the upper portion 20 to the other side is an upper strap or proximal strap 32. The strap 32 connects both sides once in place upon a patient. The proximal strap 32 may be affixed using hook and loop fasteners, snaps, buckles, or other means.

The outer support structure 24 has a vertical portion 34 extending along the calf and a horizontal portion 36 connected to the vertical portion 34 and extending rearwardly. The vertical portion 34 extends along a longitudinal axis "L". The vertical portion 34 and horizontal portion 36 comprise, in certain embodiments, a metal bar or bars.

The vertical portion 34 and horizontal portion 36 comprise, in certain embodiments a metal bar or bars attached to the outer support structure 24. The vertical portion 34 and horizontal portion 36 can be attached using rivets, screws, or other connectors. In certain embodiments, the horizontal portion 36 is omitted. In embodiments, a vertical portion and horizontal portion is formed from a thicker area or areas of plastic in the outer support structure 24. As shown in FIG. 1, the lateral hinge or joint 60 connects an upper portion of the vertical portion 44 to a lower portion of the vertical portion 34.

The vertical portion 34 can be connected to an outer support structure 44 that can have a first bar 210 and a second bar 212, the first bar being disposed at an angle with respect to the second bar. The second bar may extend toward a heel of the orthosis. The lower end 220 can be formed as a Y-shaped pair of bars. For example, a second bar 212 may extend toward the heel of the orthosis, and a third bar 213 can extend toward a toe of the orthosis.

In embodiments, a lateral side of the outer support structure 24 and the medial side of the outer support structure 24 can have a vertical portion 34 and/or horizontal portion 36. In embodiments, the medial side has a shortened vertical portion 34 comprising a metal bar, plastic material, or other supporting structure (see FIG. 2).

The upper portion 20 has an anterior offset or forward member 38 extending at a point generally mid-body. The forward member 38 is offset from the longitudinal axis L. The forward member 38 serves as the point at which stretching strap 100 is attached. Attached at this point, the stretching strap 100 is generally parallel to the longitudinal axis L and anterior to the longitudinal axis L.

The lower portion 40 has an outer support structure 44 and an inner support structure 48 attached to the shell by connectors 26. The lower portion 40 includes a molded inner boot or inner liner 50 made of a flexible material such as a pliable foam that provides pressure distribution. Extending from one side of the foot portion is a lower strap or in-step ankle strap 52 to connect both sides once in place on a patient's foot. The strap 52 may be fixed by being threaded through, for example, a loop 54, then the strap is folded upon itself and secured using hook and loop fasteners, snaps, buckles, or other means. The lower portion 40 has a sole 56 affixed to it with treads for ambulation while avoiding slipping.

The upper portion 20 and lower portion 40, are connected together by their support structures through a plurality of joints. In certain embodiments, there is a lateral hinge or outer joint 60 and a medial hinge or inner joint 62.

In embodiments, the lateral hinge or outer joint 60 is designed to permit rotation for ankle joint rotation with dorsiflexion and or plantar flexion limits. As shown, in certain embodiments, rotation is limited to 20 degrees in one direction and 20 degrees in the other direction. In embodiments, the lateral hinge 60 is limited, whereas the medial hinge 62 does not limit travel in either direction. In embodiments, either or both hinges have a mechanical stop to limit rotation. In certain embodiments, the limit on rotation in one or both directions is adjustable.

The stretching strap 100 has an upper strap or upper band 110, a lower strap or lower band 114 and a ratchet mechanism 112 connecting the upper strap and lower strap, in certain embodiments. In embodiments, the ratchet mechanism is a buckle. In embodiments, the upper strap is made of plastic or other material that is inelastic. In embodiments the lower strap is elastic and can be, for example, an elastic strap available from Gaffney Technology LLC. The upper strap is attached to the offset 38 by a connector 39. Attaching the stretching strap 100 at the offset 38 maintains more consistent mechanical advantage through dorsiflexion and plantar flexion.

The ratchet buckle 112, in embodiments, is like those used for ski and or snowboard bindings and is designed to be tightened but not loosened. In other words, the operation of the buckle allows motion of one strap with respect to the other in one direction only. The strap can be released by pushing the buckle 112, allowing the upper strap 110 to travel within the buckle 112 and releasing tension.

Figure 3:
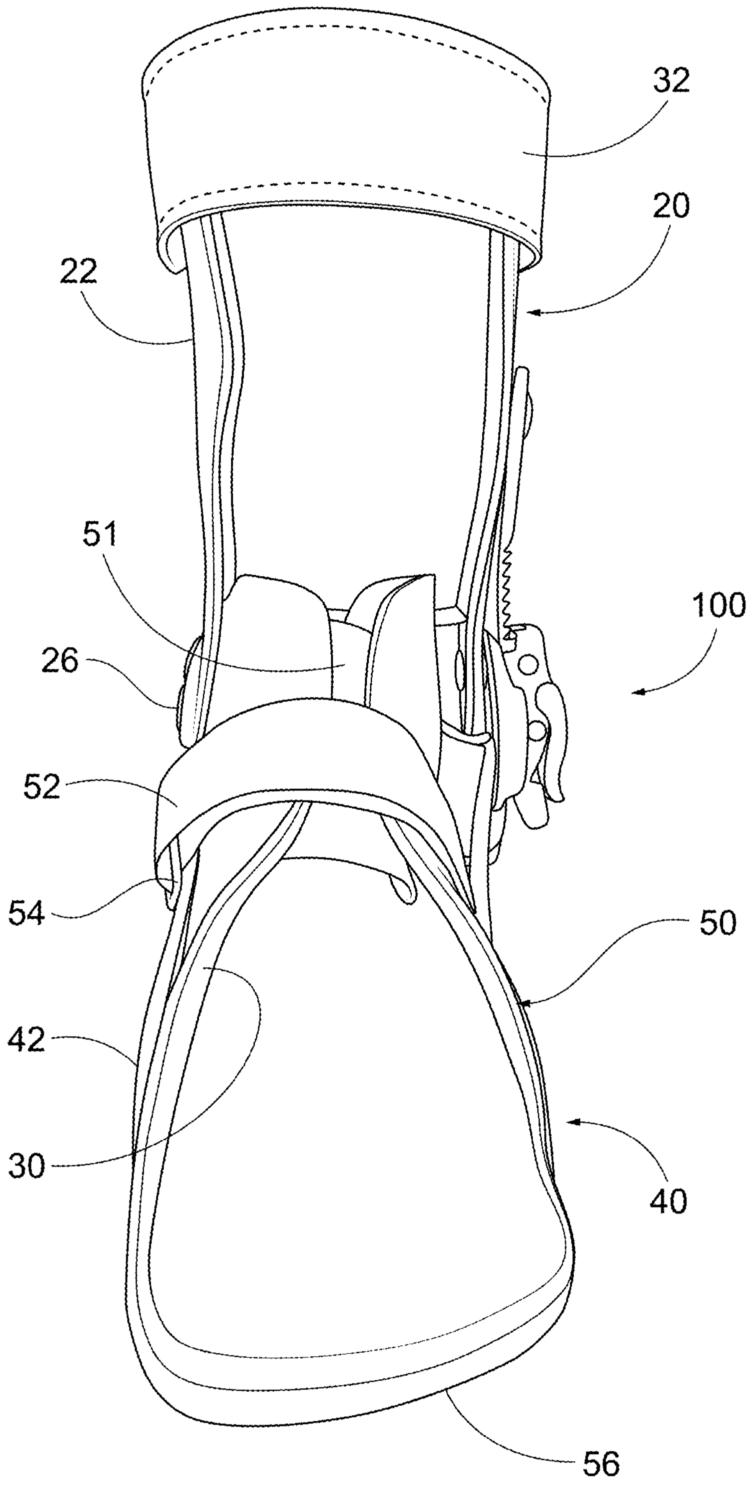
FIG. 3 is a front elevation view of the foot orthosis of FIGS. 1 and 2.
Figure 4:
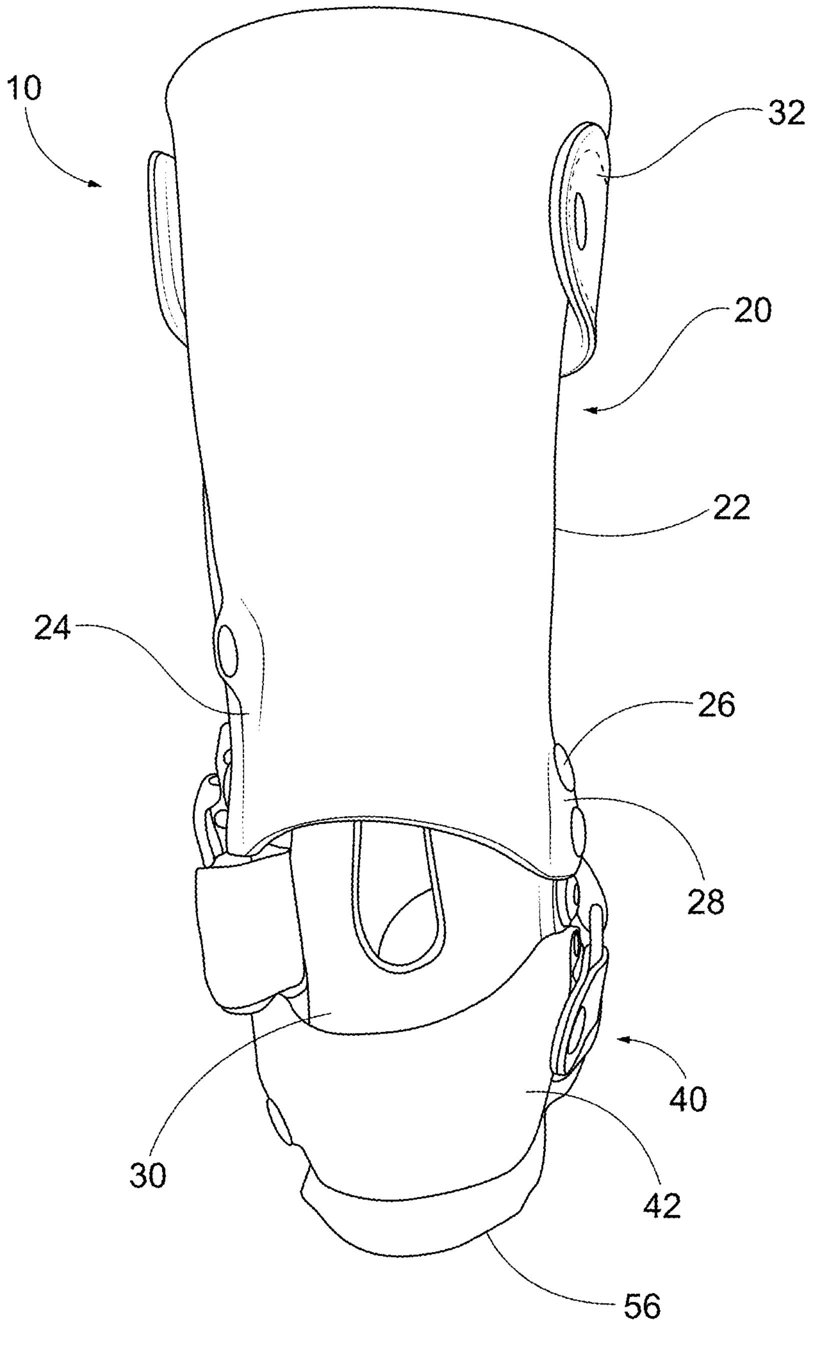
FIG. 4 is a rear elevation view of the ankle foot orthosis of FIGS. 1 through 3.
Figure 5:
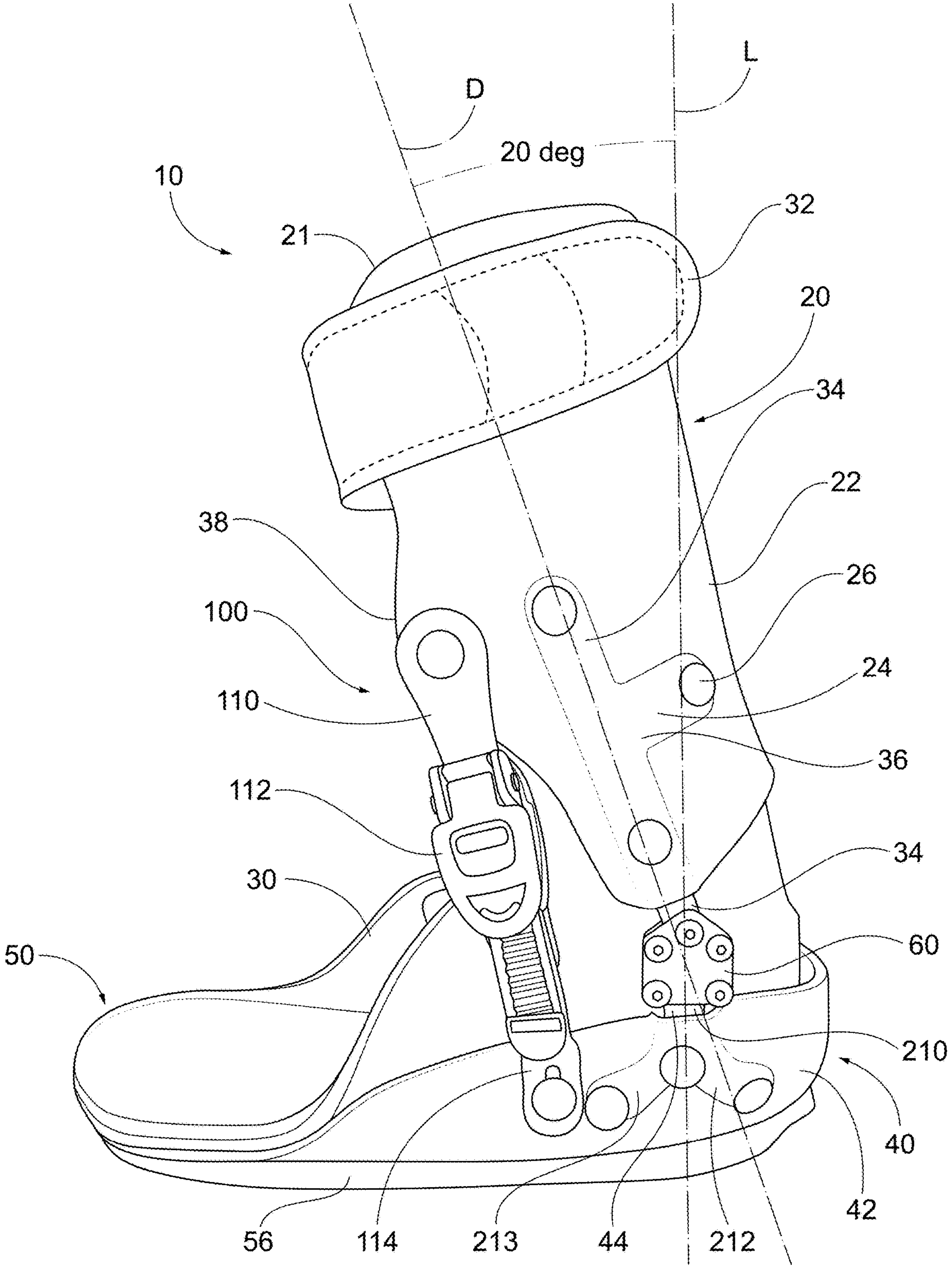
FIG. 5 is a lateral side elevation view of the ankle foot orthosis of FIGS. 1 through 4 shown in a dorsiflexion position of 20 degrees.
Figure 6:
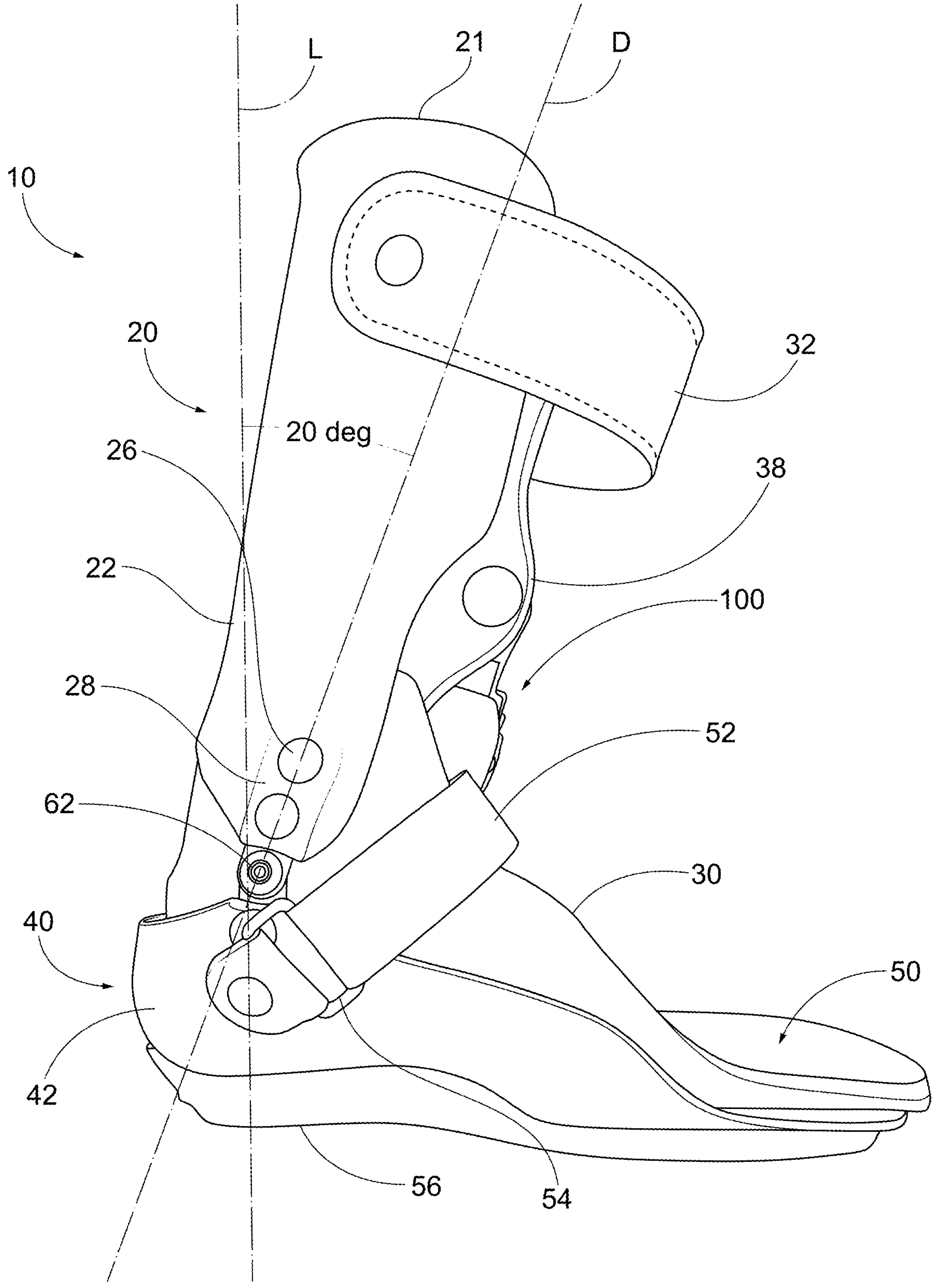
FIG. 6 is a medial side elevation view of the ankle foot orthosis of FIGS. 1 through 5 shown in a dorsiflexion position of 20 degrees.
Figure 11:
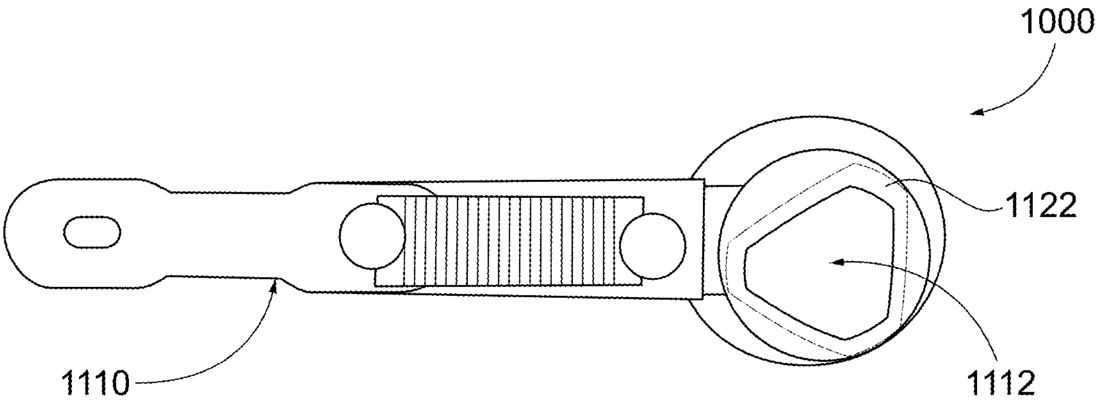
FIG. 11 is a front elevation view of a stretching strap according to a further embodiment.

In embodiments, as shown in FIGS. 3 and 11, the inner boot 50 is shown as a wrap around boot with dorsal pads 51.

Figure 7:
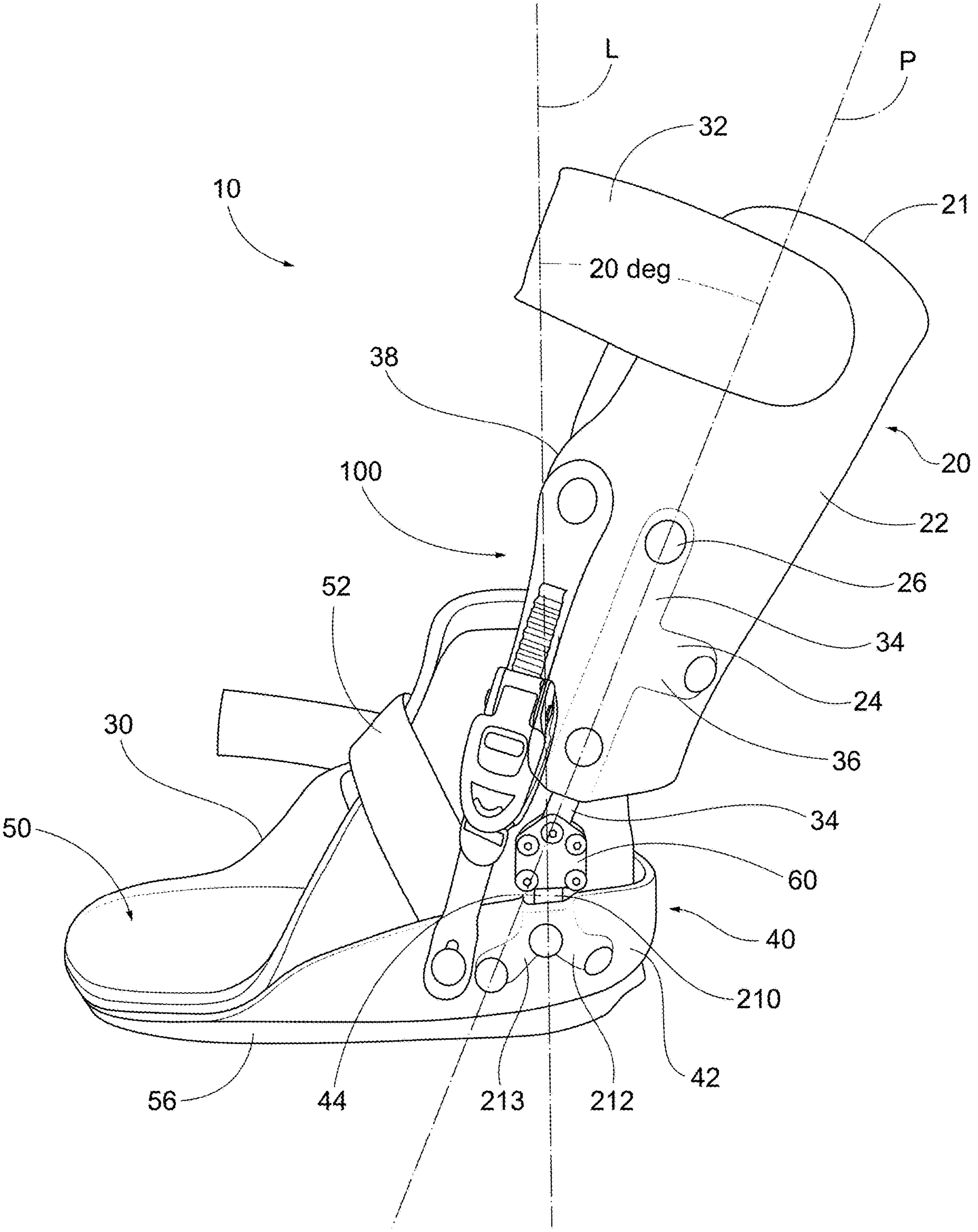
FIG. 7 is a lateral side elevation view of the ankle foot orthosis of FIGS. 1 through 6 shown in a plantar flexion position of 20 degrees.

As seen in FIG. 7, the upper portion 20 can also rotate in either direction relative to the lower portion 40 about hinges 60, 62. The vertical portion 34 is positioned along axis "P" at 20 degrees to the longitudinal axis L. In embodiments, the hinge or hinges may freely rotate when the stretching strap 100 is not in place. The stretching strap 100 adds variable resistance in plantar flexion. The stretching strap 100 assists in movement of the ankle in dorsiflexion.

Figure 8:
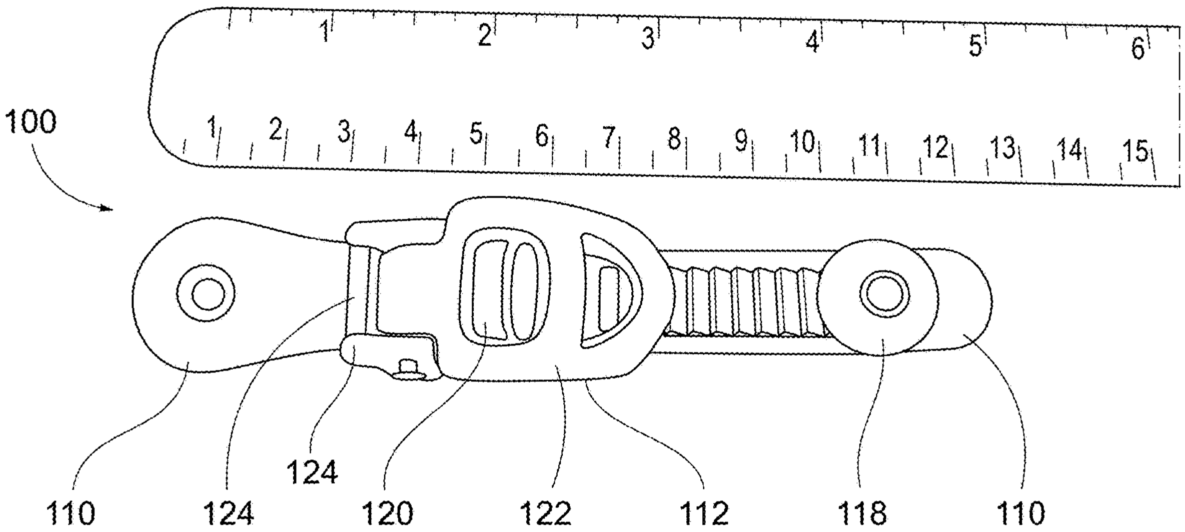
FIG. 8 is a front elevation view of a stretching strap according to an embodiment.
Figure 9:
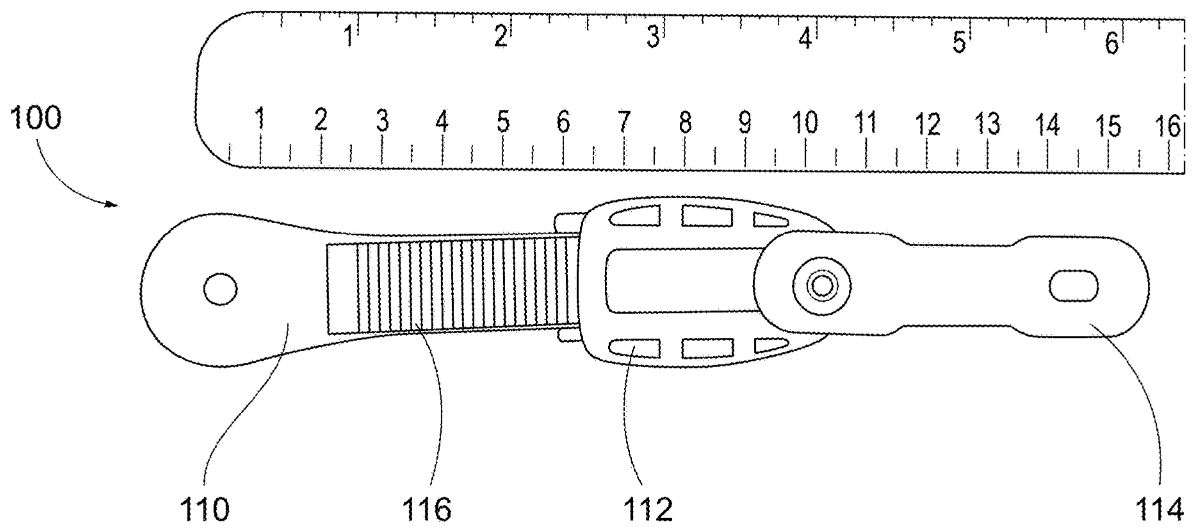
FIG. 9 is an elevation view of the stretching strap of FIG. 8.
Figure 10:
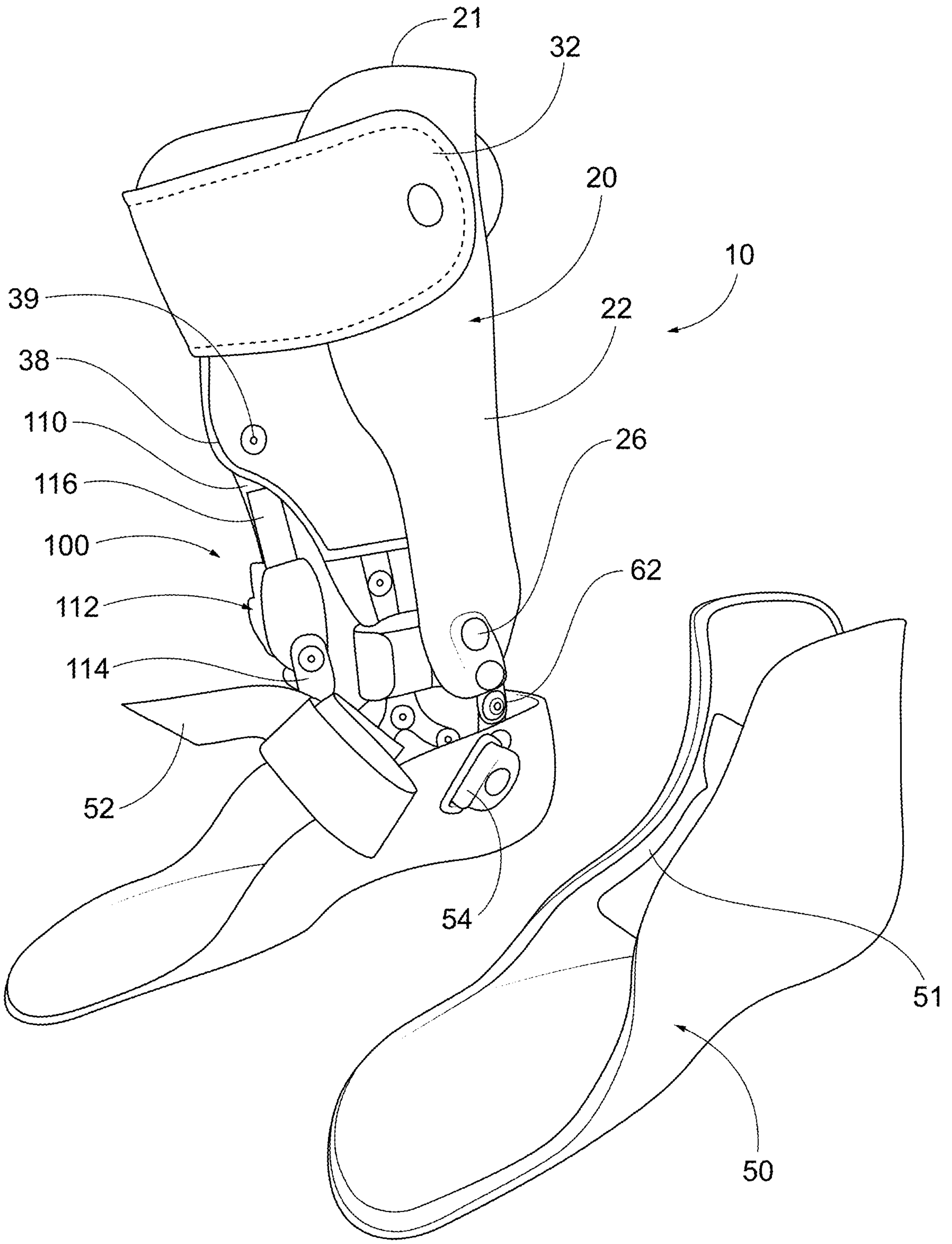
FIG. 10 is a perspective view of an ankle foot orthosis showing an inner liner removed from a lower portion of the ankle foot orthosis.

As seen in FIGS. 8 and 9, the stretching strap 100, in embodiments, has an upper strap 110, a lower strap 114, and a ratcheting buckle 112 connecting the upper strap 110 and the lower strap 114. The lower strap 114 is made of plastic that is elastic. In certain embodiments, the elastic strap is from Gaffney Technology LLC. The upper strap 110 is designed to be inelastic. Indicia 116 are provided on the upper strap 110, in embodiments. A stopper 118 is provided in embodiments to prevent the strap 110 from sliding through the ratcheting buckle 112. The ratchet buckle 112 has, in embodiments, a handle 122 that can be rotated about a hinge 124 to increase tension and, in embodiments, the buckle 112 has a button 120 can be pushed to release all tension.

In use, the ankle foot orthosis is placed upon a patient's foot and adjusted for therapy. The stretching strap AFO is designed to provide progressive and adjustable stretching to contracted musculature exhibiting range of most motion loss in the gastrocnemius and soleus muscles. Range of motion loss in this muscle group is very common in patients with a variety of diagnoses including cerebral palsy, spina bifida, muscular dystrophy, autism, idiopathic toe walking, club foot, spinal muscular atrophy, as well as many other neuromuscular and orthopedic diagnoses. The stretching strap AFO is designed to provide essential characteristics which will provide for improved compliance by patients, improved ease of donning the AFO and use, improved adjustability as needed depending on patient progress, and for improved protection of fragile bone and joint structures while isolating the stretching forces to the Achilles tendon and calf musculature.

In order to properly put on the AFO, it is very important that the patient or patient's assistant is able to position the patient's foot and lower leg into the AFO with the heel seated properly and the bones and joints held in a corrected neutral position. The stretching AFO allows for push button tension release to remove all tension from the AFO in order to facilitate this process.

When a patient's musculature is contracted with range of motion loss, it can be very difficult to properly seat the patient's foot and lower leg into an AFO. Once the patient's limb is properly seated and secured into the AFO, then the incremental tension adjustment may be applied.

Using the numeric scale which corresponds to incremental adjustments on the strap, the stretching tension will be applied up to the desired amount, taking into account the patient's comfort level. This incremental adjustment with the numeric scale allows for a continual reference point to ensure that the appropriate amount of stretch is being applied. The incremental tension adjustment also allows for an easily understandable program to increase the stretching tension over time, achieve maximum results, and maximize range of motion improvement.

The dynamic and progressive tension applied by the combination of the ratcheting component and elastomeric band also provides additional benefits. The patient will have a greater sense of freedom of movement of the affected limb and is able to actively push against the elastic band to stretch or to deal with muscle contractions occurring. The elastomeric band provides progressive stretch tension which allows for improved stretching capability even as the patient's range of motion changes during use. The elastic portion or portions elastically increase tension as they stretch. This capability of providing an adjustable and progressive stretching mechanism allows for greater patient comfort and greater patient compliance as well as greater potential range of motion improvements.

Additionally, the stretching AFO features, in certain embodiments, a dorsiflexion limit (which may consist of a Sure Step DA joint 60) or other joint with motion limiting capabilities. The limit may be set at a full 20 degrees of dorsiflexion, representing a full normal range of motion for the ankle joint, or any desired angle depending on the patient's needs. In embodiments, a hinge joint with a mechanical stop is used.

The dorsiflexion limit on the AFO ensures that the patient's ankle joint will not be stretched beyond the anatomical limitations, preventing potential injury. The dorsi flexion limit also provides a tangible "finish line" for the stretching therapy when the range of motion improves. The dorsiflexion limit helps patients and caregivers visualize the range of motion improvement being made as well as the need for further progress.

The AFO, in embodiments, has an internal inner boot which wraps around the foot and ankle. In embodiments, the inner boot is pliable and is molded to the foot. In embodiments, the inner boot is arranged to maintain the proper position of the foot and ankle in a neutral position. This can prevent stretching forces from inadvertently damaging the fragile joint structure of the subtalar joints and midtarsal joints. The molded inner boot also serves to distribute pressure created by stretching forces and the instep strap in order to prevent pressure sores and improve patient comfort and compliance.

In certain embodiments the AFO has a ratchet mechanism in the form of an adjustable knob. The stretching strap 1000, in embodiments, has a strap member 1110, and a ratcheting knob 1112. The strap member 1110 is made of plastic that is elastic. In embodiments, indicia are provided on the strap member. The ratchet knob 1112 has, in embodiments, a handle 1122 that can be rotated to increase tension.

Figure 12:
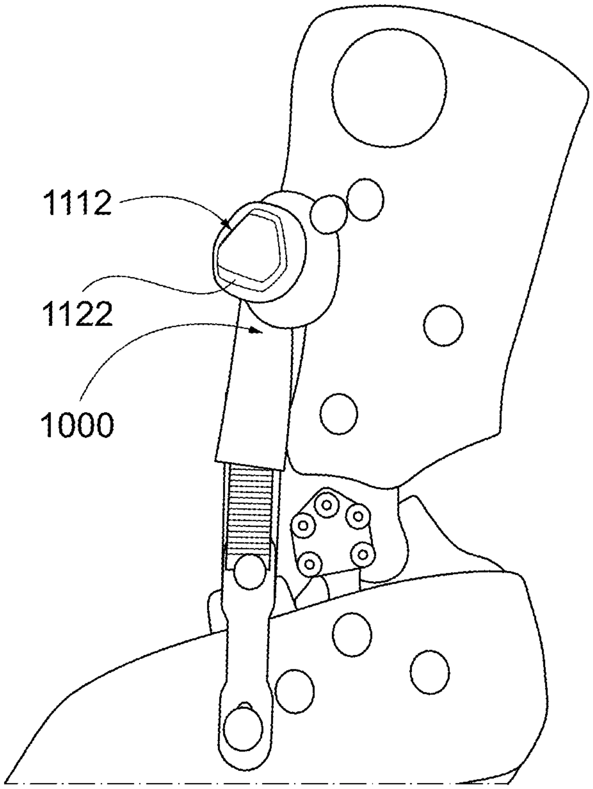
FIG. 12 is a lateral side elevation view of an ankle foot orthosis according to a further embodiment.

To begin increasing the tension on the stretching strap 1000, knob 1112 is pressed down. The knob is rotatable in a clockwise or counterclockwise direction to increase tension on the stretching strap 1000. The knob has a similar ratchet mechanism as ratchet buckle 112 to allow movement of the strap in one direction only. To release tension, the knob 1112 is pulled upwardly. See FIGS. 11 and 12. An example of such a knob is the L6 dial, which is used on the La Sportiva BOA running shoe.

In embodiments, a goniometer 300 to measure angular ankle joint position and determine how much progress is being made. See FIG. 13. The goniometer 300 is formed on the lateral hinge, in certain embodiments. The goniometer measures the angular position of the upper portion 320 relative to the lower portion 340 before the patient moves their foot, pressing against the resistance of the stretching strap. As the foot is moved, the degree of movement is shown on the goniometer 300.

The goniometer measures actual angular positioning and range of motion progress being made with the AFO, while the numeric scale on the stretching strap measures the amount of force being applied to the contracted musculature. This combination of measurement capability and incremental adjustment, give patients and medical staff the ability to track progress, and make informed decisions about whether or not the stretching strap tension is needed to be increased.

Figure 13:
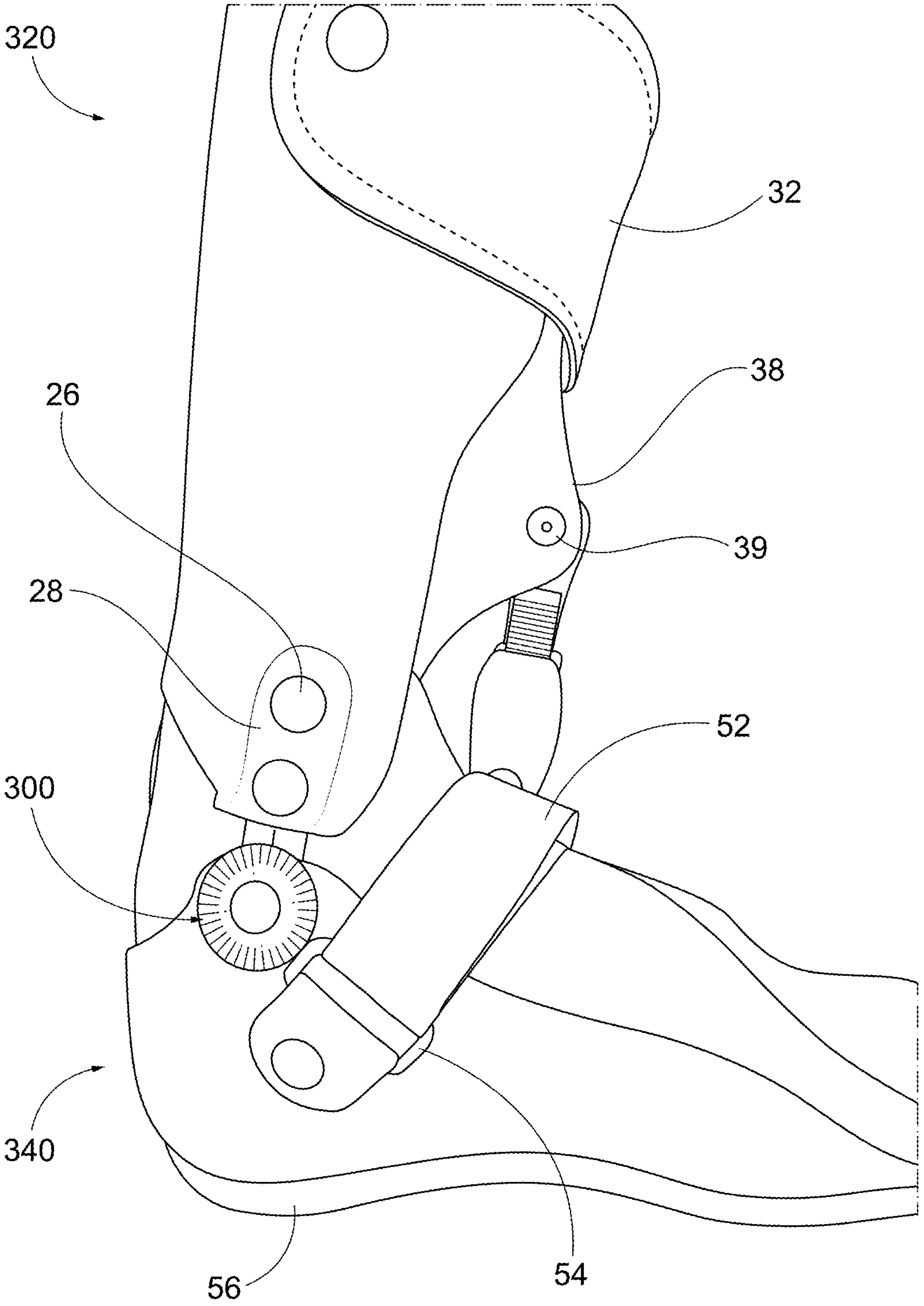
FIG. 13 is a lateral side elevation view of an ankle foot orthosis according to another embodiment.

The embodiment shown in FIG. 13 also has an anterior projection that is more pronounced, and extends farther in the anterior direction, than the anterior projection 38 shown in FIG. 1. This keeps the stretching strap components much more streamlined to the patient's leg. This allows for the use of a knee immobilizer orthosis, to be worn in conjunction with the AFO without disrupting or changing the stretching capability, or interfering with the stretching strap. In addition, all, or almost all, of the numeric scale on the stretching strap is visible.

The forces exerted with the stretching strap AFO adjustment are very inconsistent, depending on the angle of the foot to the leg. The forces exerted by the stretching strap varies, depending on the distance of the strap anterior to the ankle joint axis. When the foot is plantar flexed, the stretching strap design moves significantly closer to the ankle axis, greatly diminishing the stretching force. When the foot is Dorsiflexed, the stretching strap moves much further away from the ankle joint axis, creating a much stronger stretching force.

The location of the stretching strap provides approximately a 'parallel pull' which has a much more constant stretching force though all angles of movement of the ankle.

The anterior attachment projection shown in FIG. 13 locates the stretching strap on the anterior lateral portion of the AFO which avoids the strap getting tangled up with the opposite foot, avoids getting tangled in sheets, and minimizes bulk.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Other embodiments of the invention will be apparent to those skilled in the art from consideration of the specification and practice of disclosed herein. Although specific advantages have been enumerated, various embodiments may include some, none, or all of the enumerated advantages. It is intended that the embodiments described be considered as exemplary only, with a true scope and spirit of the invention being indicated by the appended claims. Moreover, none of the features disclosed in this specification should be construed as essential elements, and therefore, no disclosed features should be construed as being part of any claim unless expressly recited. In addition, it should be understood that any of the features disclosed in any particular embodiment may be incorporated in whole or in part any of the other embodiments.

In any interpretation of the claims appended hereto, it is noted that no claims or claim elements are intended to invoke or be interpreted under 35 USC 112(f) unless the words "means for" or "step for" are explicitly used in the particular claim.

All cited references are incorporated herein by reference hereby.

Although embodiments have been disclosed, it is not desired to be limited thereto. While various embodiments of the present disclosure have been described in detail, it is apparent that modifications and alterations of those embodiments will occur to those skilled in the art. However, it is to be expressly understood that such modifications and alterations are within the scope and spirit of the present disclosure.

The foregoing discussion of the disclosure has been presented for purposes of illustration and description. The foregoing is not intended to limit the disclosure to the form or forms disclosed herein. In the foregoing detailed description, for example, various features of the disclosure are grouped together in one or more embodiments. This method of disclosure is not to be interpreted as reflecting an intention that the claims require more features that are expressly recited in the claims. Rather, as the following claims reflect, inventive aspects lie in less than all features of a single embodiment. Thus, the following claims are hereby incorporated into this detailed description, with each claim standing on its own as a separate preferred embodiment of the disclosure. Moreover, though the present disclosure has included description of one or more embodiments and certain variations and modifications, other variations and modifications are within the scope of the disclosure such as, for example, as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to dedicate any patentable subject matter to the public.

What is claimed is:

1. An ankle foot orthosis comprising:

an upper portion configured for placement on a lower leg;

a lower portion configured for placement on a foot;

the upper portion and lower portion attached to one another by a lateral joint and a medial joint, the lateral joint and medial joint allowing rotation of the upper portion with respect to the lower portion;

a strap, at least a portion of the strap being an elastic portion, the strap having a ratchet mechanism allowing an incremental increase in stretching the elastic portion of the strap and being releasable to release all tension, a first end of the strap connected to the upper portion offset from and anterior to the lateral joint and the medial joint, and a second end of the strap connected to the lower portion offset from and anterior to the lateral joint and medial joint.

2. The ankle foot orthosis of claim 1, wherein the upper portion has a support structure having a vertical portion.

3. The ankle foot orthosis of claim 2, wherein the support structure has a lower end attached to the lower portion.

4. The ankle foot orthosis of claim 3, wherein the lower end of the support structure has a first bar and a second bar, the first bar being disposed at an angle with respect to the second bar.

5. The ankle foot orthosis of claim 3, wherein the lower end of the support structure is generally Y-shaped.

6. The ankle foot orthosis of claim 2, wherein the vertical portion comprises a metal bar.

7. The ankle foot orthosis of claim 2, wherein the support structure has a horizontal portion extending proximally.

8. The ankle foot orthosis of claim 1, wherein the ratchet mechanism has a rotatable handle.

9. The ankle foot orthosis of claim 8, wherein the handle is a rotatable knob.

10. The ankle foot orthosis of claim 1, wherein the strap has a first strap that is inelastic and a second strap that is elastic.

11. The ankle foot orthosis of claim 1, wherein the upper portion has a shell and an inner support structure.

12. The ankle foot orthosis of claim 1, wherein the upper portion has a proximal flare.

13. The ankle foot orthosis of claim 1, wherein the upper portion has a strap extending from a first side of the upper portion to a second side of the upper portion.

14. The ankle foot orthosis of claim 1, wherein the upper portion has an anterior projection offset from a longitudinal axis aligned with the lateral joint and the medial joint.

15. The ankle foot orthosis of claim 1, wherein the lateral joint limits rotation of the upper portion with respect to the lower portion to twenty degrees in a forward direction and twenty degrees in a rearward direction.

16. The ankle foot orthosis of claim 1, further comprising an inner boot.

17. The ankle foot orthosis of claim 1, wherein the ratchet mechanism is a ratchet buckle having a button for releasing all tension when the button is pushed.

18. The ankle foot orthosis of claim 1, wherein at least one of the lateral joint and the medial joint has a goniometer.

19. The ankle foot orthosis of claim 1, wherein the upper portion has an anterior projection, the first end of the strap being connected to the anterior projection.

* * * * *